United States Patent [19]
Wijts

[11] Patent Number: 5,084,243
[45] Date of Patent: Jan. 28, 1992

[54] TURRET STERILIZER

[75] Inventor: Corneel C. Wijts, Saratoga, Calif.

[73] Assignee: FMC Corporation, Chicago, Ill.

[21] Appl. No.: 406,011

[22] Filed: Sep. 12, 1989

[51] Int. Cl.$^5$ ............................ A61L 2/08; A61L 2/24
[52] U.S. Cl. .................................. 422/26; 422/38;
    422/302; 422/304; 99/361; 99/468; 426/521
[58] Field of Search ............... 422/26, 38, 302, 304;
    99/361, 468, 470, 477, 479; 426/233, 407, 412,
    521; 53/426, 167

[56] References Cited
U.S. PATENT DOCUMENTS
| | | | |
|---|---|---|---|
| 4,590,734 | 5/1986 | Ueda | 53/167 |
| 4,683,701 | 8/1987 | Rangwala et al. | 422/304 |
| 4,788,811 | 12/1988 | Kawajin et al. | 53/426 |

Primary Examiner—Robert J. Warden
Assistant Examiner—Laura E. Collins
Attorney, Agent, or Firm—A. J. Moore; R. C. Kamp; R. B. Megley

[57] ABSTRACT

A batch sterilization system is disclosed having a plurality of retorts mounted on at least one indexable turret which sequentially and simultaneously indexes one retort with a loader for receiving containers to be sterilized, while a second retort with sterilized containers therein is indexed with an unloader for unloading. A second embodiment includes a pair of loader/unloaders for loading and unloading a first product in first retorts and a second product in the other retorts.

24 Claims, 3 Drawing Sheets

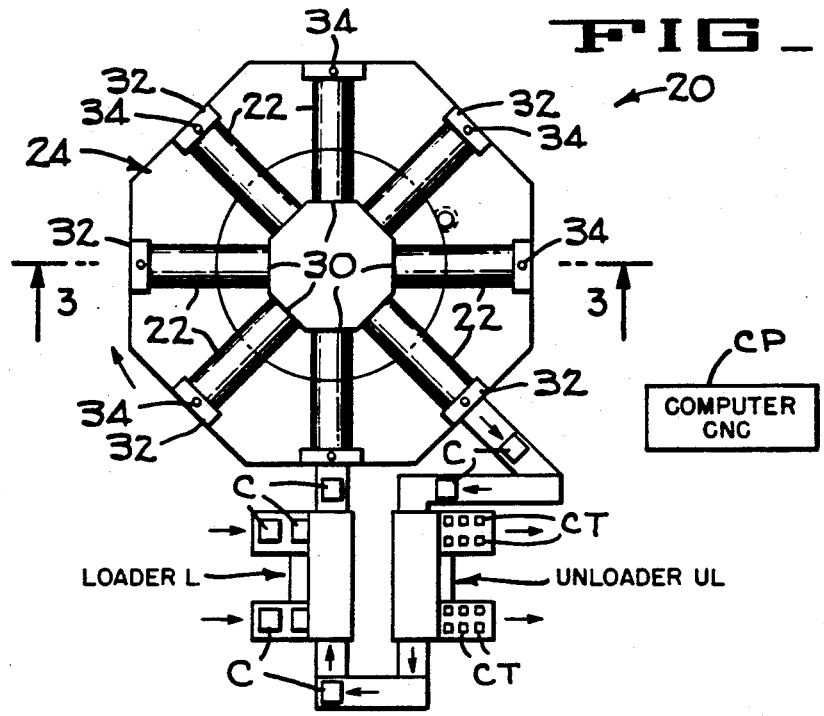
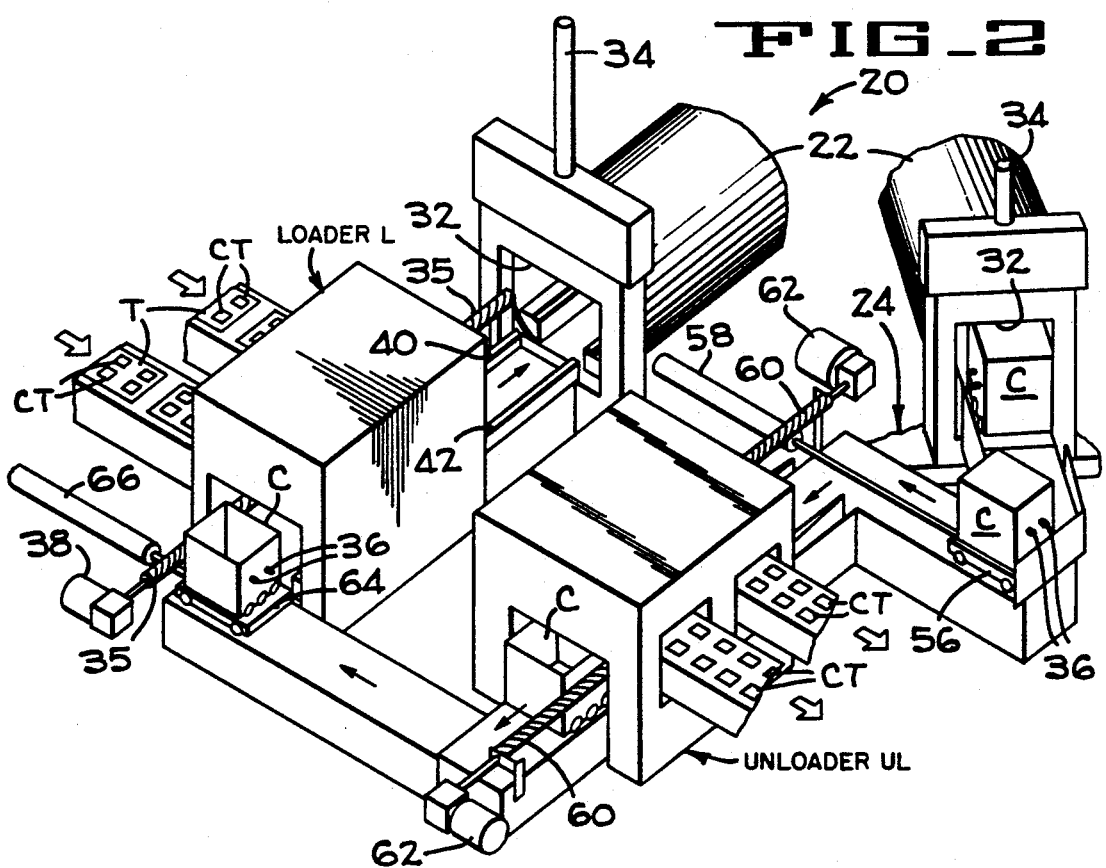

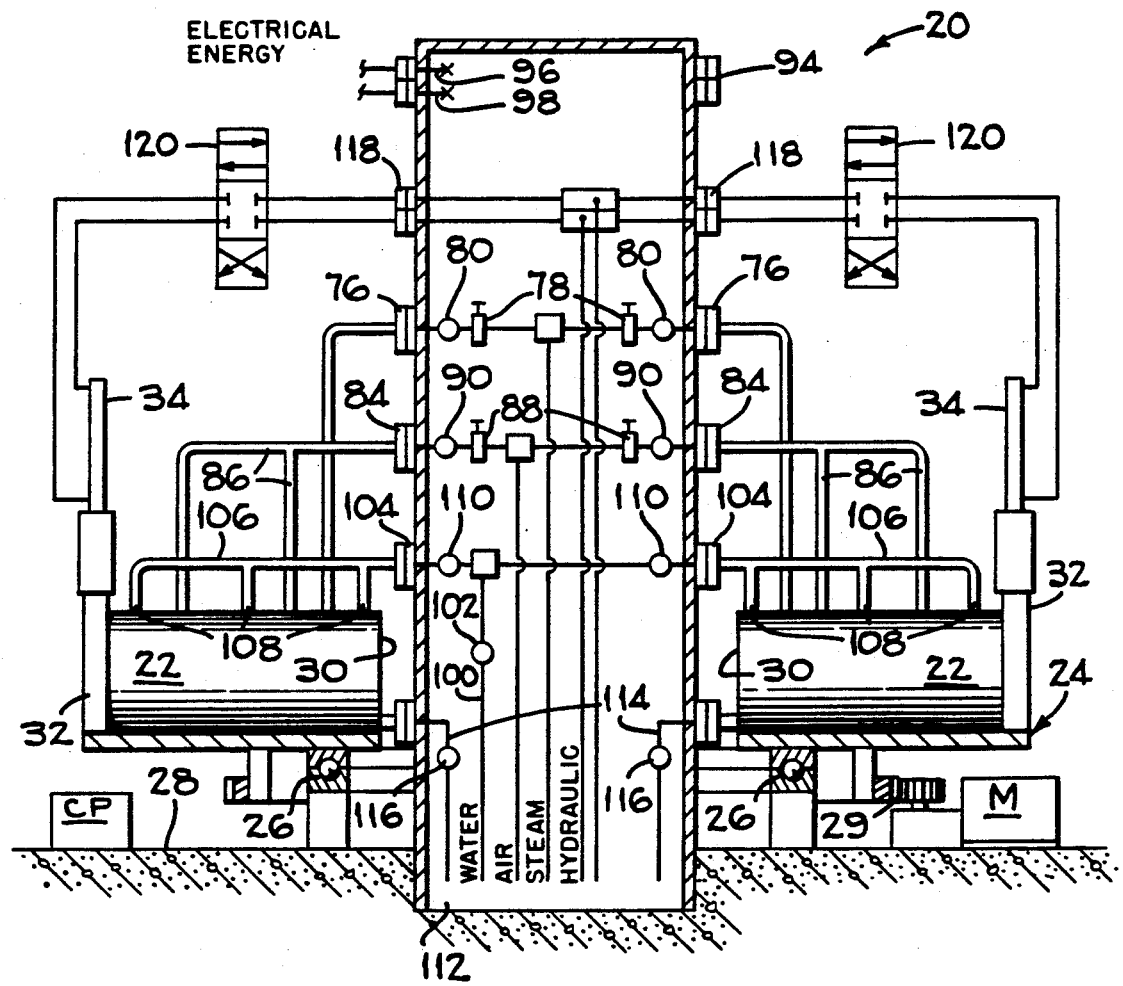
FIG_3

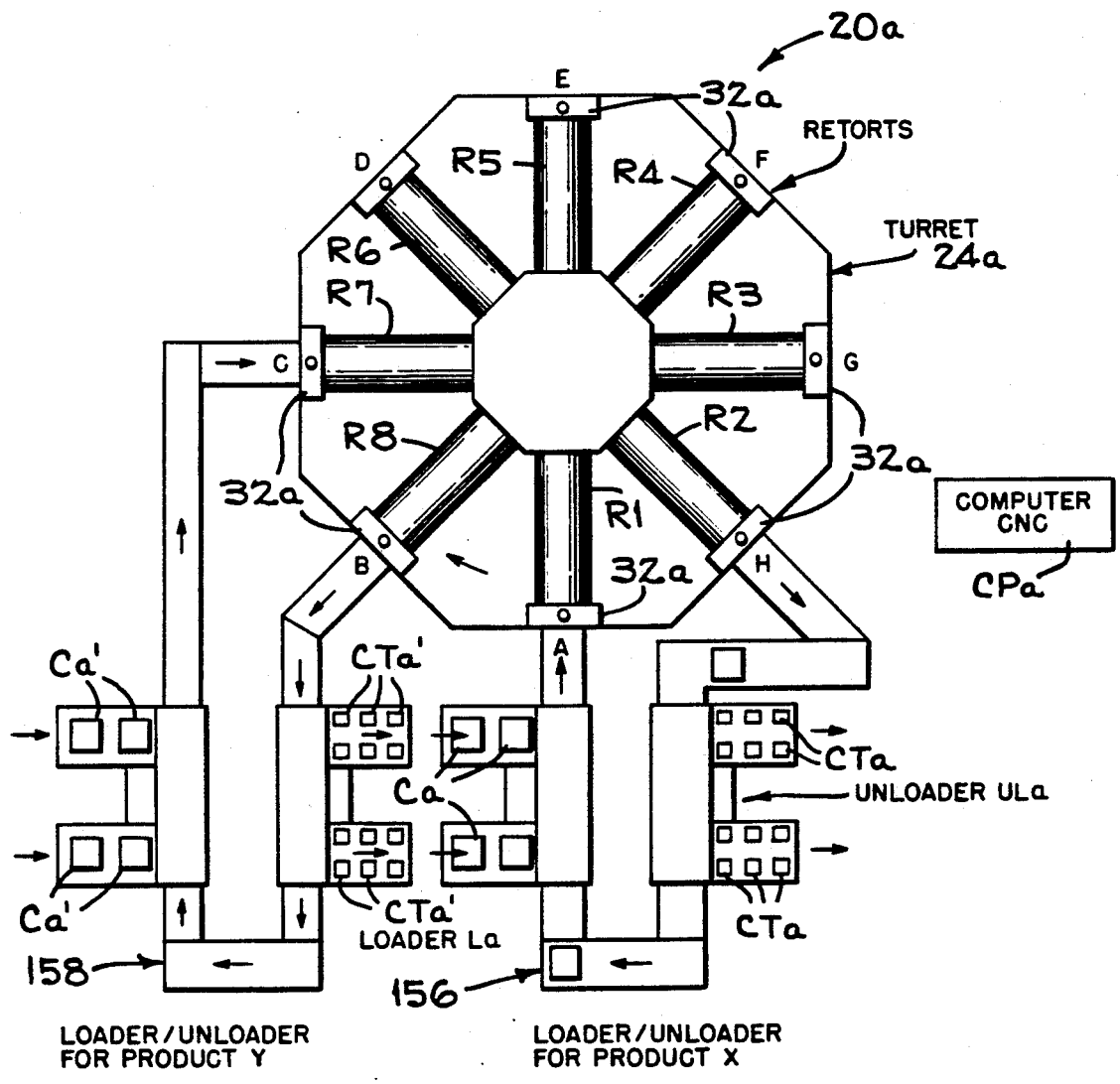
FIG_4

TURRET STERILIZER

CROSS REFERENCE TO RELATED APPLICATION

The present invention is similar to my application entitled Batch Sterilization System, Ser. No. 07/346,443 filed on Apr. 24, 1989.

BACKGROUND OF THE INVENTION

1. Field of the Invention

The present invention pertains to sterilizing systems and more particularly relates to a plurality of batch type retorts mounted on an indexable turret for simultaneously moving one retort into position to receive container filled cars to be sterilized from a loader, and to simultaneously discharge sterilized containers from a second retort into an unloader.

2. Description of the Prior Art

Batch type sterilizers or retorts such as that disclosed in Mencacci U.S. Pat. No. 4,164,590 are well known in the art and are adapted to receive and discharge a plurality of containers within supporting cars through a door at one end of each retort.

A continuous pressure cooker and cooler is disclosed in Mencacci U.S. Pat. No. 4,196,225 and illustrates container filled cars or carts which are moved from one end to the other end of a continuous cooker and cooler while cooking and thereafter cooling containers being processed.

Commercially available batch type sterilizers such as FMC Model CFS are also used for sterilizing food products in cans, jars, pouches, plastic trays and other product filled containers.

European Patent Application Publication No. 0075531 discloses a sterilizing system which includes means for filling and sealing articles in containers, loading trays with the sealed articles therein into stacks, and then conveying the stacks through a sterilizer and thereafter removing the sterilized containers with the aid of a conveying system.

Conventional container receiving cars, loaders, unloaders, and car conveying means are disclosed in Creed et al U.S. Pat. No. 4,646,629.

Piegza U.S. Pat. No. 3,776,257 discloses the use of water as a heating medium in retorts and the use of power means for opening and closing retort doors.

Certain faults are present in the sterilizing industry primarily due to demand for more and more containers to be sterilized. An increase in the use of sterilized food products or the like indicates that sterilization systems should be designed to conserve space and also be automated. Although the containers have usually been loaded and unloaded from cars automatically, at the present time the cars are usually transported between these loaders/unloaders and the retorts by fork lifts or automatically guided vehicles. As the prior art sterilization system becomes bigger, this transport function becomes quite complex and labor intensive. It also becomes difficult to keep track of sterilized and unsterilized containers in the plurality of cars after they have been removed from present prior art systems.

SUMMARY OF THE INVENTION

In accordance with the present invention, the above faults are rectified by mounting a plurality of radially disposed retorts on an indexable, rotatable turret that is indexed in alignment with conventional loaders and unloaders. Water, steam, air, hydraulic fluid, and electrical services are connected to the retorts through rotary couplings concentric with the axis of rotation of the turret. The retorts are arranged so that adjacent retorts will simultaneously index with adjacent loaders and unloaders when held stationary. If batches of containers have two or more products which require different processing temperatures and pressures are being sterilized in the retort, two or more loader/unloaders are provided to feed different products into different retorts supported on the turret. This permits processing two different products at the same time and at different temperatures and pressures without danger of mixing the two products together.

DESCRIPTION OF THE DRAWINGS

FIG. 1 is a diagrammatic plan of a first embodiment of the invention.

FIG. 2 is a perspective diagrammatically illustrating a loader, an unloader, and conveyors in positions to move unprocessed containers within cars into one retort and to receive processed containers from another retort for unloading by the unloader.

FIG. 3 is a diagrammatic vertical section taken along lines 3—3 of FIG. 1 diagrammatically illustrating conventional drive means for indexing the retort; and further illustrating means for controllably directing water, steam, air, hydraulic fluid and electrical services into the retorts, only two retorts being illustrated.

FIG. 4 is a diagrammatic plan of a second embodiment of the invention which processes and maintains two different products segregated while feeding, sterilizing and discharging sterilized containers.

DESCRIPTION OF THE PREFERRED EMBODIMENT

A first embodiment of the turret sterilizer 20 (FIGS. 1-3) of the present invention includes a plurality of equally spaced retorts 22 mounted on an indexable turret 24 supported by bearings 26 (FIG. 3) on a floor 28 and driven by a motor M and drive train 29. Each retort 22 includes a tubular body having its inner end closed by an end closure 30 and having an outer end which is adapted to be opened or closed by a door 32 which is actuated by a hydraulic cylinder 34. A conventional loader L is provided to load containers CT into cars C; and a conventional unloader UL is provided to unload processed containers CT from the cars C.

The conventional loader L, unloader UL, trays T, and cars C may be of the type illustrated by Assignee's Creed et al U.S. Pat. No. 4,666,722 which issued on Nov. 19, 1987.

The loader L (FIG. 2) receives trays T of containers CT to be loaded into empty cars C. After the cars are loaded the cars are conveyed into one of the open retorts 22 at a feed station by a screw conveyor 35 which engages a set of pins 36 on opposite sides of each car C (only one set of pins being shown in FIG. 2). A gear motor 38 drives the screw conveyor 35 and first advances the filled trays T into position to be loaded into the cars C. After the cars C are loaded, they are advanced along a V-shaped track 40 and a flat track 42 into the open retort 22. Similar driven screw conveyors (not shown) are positioned in each retort 22 for moving the cars along tracks 44,46 into the retort 22. Thereafter an open door 32 on the retort 22 is closed by a hydraulic cylinder 34.

When one retort 22 is being loaded, another retort is being unloaded by a driven screw conveyor (not shown) similar to the screw conveyor 35. Each car C is intermittently moved onto a cart 56 which is connected to a hydraulic cylinder 58 which moves the car C into position to have a set of pins 36 mesh with a screw conveyor 60 which is driven by a gear motor 62. The gear motor 62 intermittently advances the car C into the unloader UL at which time the processed containers CT are removed from the car C and the empty cars are moved onto a cart 64 that is alternately moved by a hydraulic cylinder 66 from a receiving position adjacent the unloader UL to a position adjacent the loader L, and thereafter repeats the cycle.

Steam, air and water are controllably directed into the several retorts 22 at predetermined time intervals. The different components of the turret sterilizer 20 are preferably controlled by the computer CP or programmable controller with the aid of conventional sensors and controls.

More particularly, steam may be directed into the several retorts 22 from a source of steam (not shown) through a swivel joint 76 (FIG. 3), through on-off valves 78 and temperature control valves 80 under the control of the computer CP. The computer closes the on-off valve 78 when the retort gates 32 are opened to receive or discharge container filled cars; and also closes the valves 78 and gates 32 when the retorts are in their cooling cycles. When the containers are in their sterilizing cycle, the on-off valves 78 are opened and the temperature controlled valves 80 are controlled by the computer CP to first control the gradual rise in temperature, to then retain the steam at sterilizing temperature during cooking, and will thereafter gradually decrease the flow of steam into the retorts 22 prior to cooling at which time the on-off valves are closed.

During sterilization and initial cooling, it may be desirable to use a steam-air mixture rather than saturated steam as the heating medium depending upon the type of containers CT being used, for example, plastic or glass containers, and the product within the containers. A high pressure source of air is directed through a swivel joint 84 through air conduit systems 86 (only two being shown), each having an on-off air valve 88 and a pressure control valve 90 therein. When air is used, the on-off air valve 88 is open during sterilization and may remain open during cooling until the pressure within the containers being processed is below atmospheric pressure. The on-off air valve 88 and the pressure control valve 90 are controlled by the computer CP and conventional electrical controls and sensors (not shown). It will also be understood that sprays of hot water followed by sprays of cooling water may be used as the heating and cooling mediums, and that air or steam/air mixtures can be used to provide an overriding pressure.

Electrical energy is directed into the several electrically controlled components by a rotary electrical coupling 94 and conduits 96,98 which direct the electrical energy into the different controls, only two conductors being illustrated.

After the contents of the containers have been sterilized, cooling water is directed into the closed retorts 22 from a source of water directed into a conduit 100 and controllable valve 102 through a swivel joint 104 into a plurality of headers 106, each of which directs cooling water through branch conduits 108 into associated retorts 22. Each header has a control valve 110 therein to regulate the volume of cooling water entering the retorts 22 and cars C therein. The cooling water is discharged from the retorts into a trough 112 through conduits 114 having control valve 116 therein which are controlled by the computer to maintain the proper level of coolant in the cars C until the containers are adequately cooled.

When it is desired to open and close the retort doors 32, hydraulic fluid is directed through a swivel joint 118 and directional control solenoid valve 120 which receives signals from the computer CP to direct hydraulic fluid into the cylinders 34 to open and close the doors when in alignment with the two retorts 22 indexed with the loader L and unloader UL (FIG. 2).

Having reference to FIG. 4, which diagrammatically illustrates a sterilizer 20a which is capable of sterilizing two different products which may require different temperatures and pressures. Since the turret sterilizer 20a includes components similar to that of the first embodiment of the invention, the components of the turret sterilizer 20a which are equivalent to those of the first embodiment will be assigned the same numerals followed by the letter "a".

The turret sterilizer 20a includes a plurality of rotorts R1-R8, each having a door 32a mounted on an indexable turret 24a. As illustrated in FIG. 4, a first loader/unloader 156 is similar to that illustrated in FIGS. 1 and 2, but is provided to sterilize first containers CTa which are fed into rotorts R1, R2, and R5, R6 when at station A and are discharged from said retorts when at station H. A second loader/unloader 158 is provided to handle second containers CTa' filled with a different product which may or may not require different sterilizing temperatures and pressures. The second product is loaded into and unloaded from retorts R3, R4 and R7, R8, respectively. The loading of containers CTa' takes place at station C, and the sterilized containers CTa' are discharged at station B.

When starting the sterilization operation it will be assumed that all retorts R1-R8 are empty and that the retort door 32a at inlet stations A and C are open. A plurality of cars Ca filled with a first batch of containers CTa are then conveyed into retort R1 at station A and the retort door 32a of retort R1 is closed and a sterilizing medium such as hot water, steam, or a steam-air mixture is directed into retort R1 through circuits similar to those illustrated in FIG. 3. Sterilization and thereafter cooling of the containers in retort R1 continues until retort R1 is indexed to station H at which time door 32a is opened and the processed containers Ca are discharged into the unloader ULa.

At the same time that retort R1 is being loaded at Station A, a plurality of containers CTa' in cars Ca' are conveyed into retort R7 at station C, and the associated door is closed, at which time sterilization of the containers CTa' begins.

The turret 24a is then indexed one step in the direction of the arrow thereby positioning empty retort R2 at station A for receiving cars Ca filled with containers CTa. The associated door 32a is then closed and sterilization followed by cooling will then occur in retort R2. At the same time empty retort R8 is indexed at station C and recovers cars Ca' filled with said second batch of containers CTa'. The associated retort door 32a is then closed permitting sterilization and thereafter cooling of the second batch of containers CTa' before subsequent discharge at station B.

Thus, the single step indexing of turret 24a sequentially fills retorts R1, R2,-R5, R6 with the first product at station A and subsequently discharges the first product at station H. Similarly, indexing of the turret sequentially fills retorts R7, R8 and R3, R4 at station C with containers CTa' filled with a second product to be sterilized at station C and subsequently discharges the sterilized and cooled second product at station B.

Thus, after all retorts R1-R8 have been initially filled with their associated products CTa or CTa', each indexing movement of the turret 24a will move retorts handling containers CTa into station H to discharge cars Ca with the sterilized and cooled containers CTa therein, and to receive cars Ca filled with containers CTa to be sterilized at station A. At the same time the second cars CA' with the second containers CTa' to be sterilized therein are loaded into the retort at station C, and the sterilized containers CTa' are discharged at station B. Thus, sterilization and subsequent cooling of the containers CTa and CTa' takes place during all indexing movements except during one indexing movement of the turret. With eight retorts on the turret as illustrated in FIG. 4, sterilizing followed by cooling occurs during 315° of rotation of the turret.

As in the first embodiment of the invention, the heating medium may be steam, a steam/air mixture, or sprays of hot water may be used as the heating medium. Air or a steam/air mixture can be used to provide the necessary overriding pressure to prevent damage to the containers.

A computer CPa and circuitry similar to that disclosed in FIG. 3 of the first embodiment controls the movement of the turret 24a and processing fluids and times.

From the foregoing description it is apparent that the turret sterilizers of the present invention are capable of minimizing floor space by using a plurality of retorts mounted at evenly spaced intervals on an indexable turret. Cars containing the containers to be sterilized are moved into the retorts by conveying systems. A heating medium such as hot water, steam, or a steam-air mixture is directed into the retorts and may be subjected to an overriding air pressure during sterilization for controlling the pressure within the retorts and within the contents of the containers. The containers are then cooled by flooding or spraying cooling water thereon prior to the discharging of the containers from the retorts, and the processed containers are thereafter removed from the cars. In the second embodiment of the invention two different products may be sterilized in different retorts on the turret sterilizer. If a very large volume of containers, or two or more types of products are to be sterilized, two or more turret sterilizers may be mounted above each other on different floors so that the most desirable cooking times, pressures, and temperatures can be used for sterilizing each product.

Although the best mode contemplated for carrying out the present invention has been herein shown and described, it will be apparent that modification and variation may be made without departing from what is regarded to be the subject matter of the invention.

What is claimed is:

1. In a container sterilizing apparatus, the combination of:
    means defining a turret;
    means defining a plurality of retorts on said turret;
    means defining a door on each retort;
    means for intermittently indexing the turret for moving each retort in turn into a feed position for receiving containers to be sterilized while moving other retorts into container discharging positions for discharging containers after being sterilized and cooled;
    means for opening said retort doors when said retorts are in said feed position and to retain said doors open until after said retorts receive said containers to be sterilized at said feed stations and for thereafter closing said doors;
    means for directing a sterilizing medium into said closed retorts as said retorts move through a portion of the distance between said feed position and said container discharging position; and
    means for directing a cooling medium into said closed retorts while the retorts are moved through the remaining distance between said container receiving position and said container discharging position.

2. An apparatus according to claim 1 wherein said sterilizing medium is steam.

3. An apparatus according to claim 1 wherein said sterilizing medium is a steam-air mixture.

4. An apparatus according to claim 1 wherein said cooling medium is water.

5. An apparatus according to claim 1 and additionally comprising cars for supporting said containers and wherein said cooling medium is water directed into said cars.

6. An apparatus according to claim 1 and additionally comprising a computer for controlling the actuation of said means for indexing said turret, said means for opening and closing said retort doors, said means for directing said sterilizing medium into said retorts, and said means for directing cooling water into said retorts.

7. An apparatus according to claim 1 and additionally comprising:
    means defining a plurality of cars for supporting said containers;
    loader means for loading the containers into said cars and thereafter loading the cars into said retorts;
    unloader means for receiving said cars and sterilized and cooled containers from said retorts and removing the containers from said cars; and
    conveying means for conveying the empty cars into said loader means for loading a plurality of containers to be processed therein.

8. In a method of sterilizing and thereafter cooling a product in filled containers within cars comprising the steps of:
    supporting a plurality of equally spaced retorts on a turret with each retort having a door;
    intermittently indexing the turret for simultaneously and progressively aligning each retort in turn with an unloader and a loader;
    opening the door of each retort in turn when aligned with the unloader;
    maintaining the retort door open until after the retort is indexed with said loader for receiving at least one car having containers to be sterilized therein;
    closing said door after said at least one car has been loaded;
    directing a sterilizing medium into each loaded retort as said loaded retorts are progressively indexed toward said unloader for sterilizing the product in the containers;

directing a cooling medium into each retort for cooling the product to a temperature below the boiling temperature at atmospheric pressure before each retort is indexed with said unloader;

opening the door of the retort indexed with the unloader;

conveying the cars with sterilized and cooled containers therein into said unloader;

unloading the containers from the cars; and moving said at least one empty car into said loader for loading another batch of the containers to be processed therein.

9. A method according to claim 8 wherein the sterilizing medium is steam.

10. A method according to claim 8 wherein the sterilizing medium is a steam-air mixture.

11. A method according to claim 8 wherein said sterilizing medium is water subjected to an overriding air pressure.

12. A method according to claim 9 wherein the cooling medium is water.

13. A method according to claim 12 wherein the cooling water is directed into said cars for submerging the containers.

14. A method according to claim 12 wherein the cooling water is sprayed over the containers.

15. A turret sterilizer for maintaining a first and a second product separate from each other during sterilization and cooling, comprising:

means defining a turret;

means defining a plurality of first and second retorts mounted on said turret, each having a door movable between an open and closed position;

means defining a first loader/unloader for loading a first product to be sterilized and cooled when in a plurality of first retorts and to simultaneously unload the sterilized and cooled first product from another of said first retorts;

means defining a second loader/unloader for loading a second product to be sterilized and cooled when in a plurality of second retorts and to simultaneously unload the sterilized and cooled second product from another of said second retorts; and power means for indexing said turret one step at a time for simultaneously loading the first and second products and thereafter unloading the sterilized first and second products from said associated retorts.

16. An apparatus according to claim 15 wherein said first unloader, said first loader, said second unloader, and said second loader are positioned to register with adjacent retorts at which time the first and second sterilized and cooled products are simultaneously discharged from their retorts and simultaneously therewith first and second products to be processed are loaded within empty first and second empty retorts, thus assuring that heat treatment of the first and second product will take place during all indexing movements of the turret except when the unloaded retorts are moving one step between their unloading position to their loading position.

17. A turret sterilizer for maintaining a first and second product separate from each other during sterilization and cooling, comprising:

means defining a turret;

means defining a plurality of first and second retorts mounted on said turret, each having a door movable between an open and a closed position;

means for sterilizing and thereafter cooling said first and second product while in said first and second retorts;

means defining a first loader/unloader for loading a batch of the first product to be sterilized into one of said first retorts and to simultaneously discharge sterilized and cooled products from another one of said first retorts;

means defining a second loader/unloader for loading a batch of second products to be sterilized into one of said second retorts and to simultaneously receive sterilized and cooled products from another one of said second retorts; and power means for indexing said turrets one step at a time for each load/unload cycle, for opening and closing said retort doors when indexed with said loader/unloader means.

18. An apparatus according to claim 17 wherein said first and second products are enclosed in batches of containers which are loaded into separate cars prior to being loaded into associated ones of said retorts handling the same products.

19. An apparatus according to claim 17 wherein sterilizing and subsequent cooling of the associated products take place for each retort during the complete cycle of operation of the turret less one indexing step of the turret between the unloading and loading of the retort.

20. An apparatus according to claim 18 wherein containers containing a sterilized and cooled first product is discharged from one retort at an unloading station while unprocessed containers containing the first product are simultaneously being loaded into a next adjacent retort.

21. An apparatus according to claim 20 wherein containers containing a sterilized and cooled first product in first containers are being unloaded from a retort next to the retort being loaded with containers containing the first product, and wherein processed containers containing the second product are being unloaded while the next adjacent empty retort is being loaded with containers containing the second product.

22. An apparatus according to claim 21 wherein said first and second products are fed into and removed from their associated retorts simultaneously.

23. A method of maintaining a first and second product separate from each other while being sterilized and cooled when within a plurality of first and second retorts mounted on an indexable turret, comprising the steps of:

intermittently indexing the turret one step at a time while directing a sterilizing medium followed by a cooling medium into each first and second retorts at temperatures and pressures which will sterilize and thereafter cool the first and second products within the first and second retorts, respectively;

filling a first retort with a first batch of product to be sterilized and cooled while simultaneously discharging a previously sterilized batch of said first product from a next following retort containing the first product;

filling a second retort with a second batch of products to be sterilized and cooled while simultaneously discharging a previously sterilized and cooled batch of said second product from a next following retort containing the second product; and sealing said first and second retorts after said first and second retorts have been filled with said first and second batches of products respectively for repeating the cycle of operation.

24. A method according to claim 23 wherein said first and second retorts when empty and in alignment with a first and a second loader are filled with said first and second batches of products simultaneously.

* * * * *